(12) United States Patent
Malinin

(10) Patent No.: US 7,371,260 B2
(45) Date of Patent: May 13, 2008

(54) METHOD AND INSTRUMENTATION FOR THE PREPARATION AND TRANSPLANTATION OF OSTEOCHONDRAL ALLOGRAFTS

(75) Inventor: Theodore I. Malinin, Key Biscayne, FL (US)

(73) Assignee: Biomet Sports Medicine, Inc., Warsaw, IN (US)

( * ) Notice: Subject to any disclaimer, the term of this patent is extended or adjusted under 35 U.S.C. 154(b) by 0 days.

(21) Appl. No.: 11/259,749

(22) Filed: Oct. 26, 2005

(65) Prior Publication Data

US 2007/0093896 A1  Apr. 26, 2007

(51) Int. Cl.
  *A61F 2/38* (2006.01)
  *A61F 5/00* (2006.01)
  *A61B 17/00* (2006.01)

(52) U.S. Cl. .............. 623/14.12; 606/80; 606/86; 606/87; 606/96; 600/567

(58) Field of Classification Search ......... 623/14.12, 623/23.6, 23.61, 23.62, 23.63, 908, 919, 623/923; 600/567; 606/86, 87, 96, 80
See application file for complete search history.

(56) References Cited

U.S. PATENT DOCUMENTS

| 3,835,849 | A | * | 9/1974 | McGuire ............ | 606/96 |
|---|---|---|---|---|---|
| 4,904,259 | A | | 2/1990 | Itay | |
| 5,053,050 | A | | 10/1991 | Itay | |
| 5,513,662 | A | | 5/1996 | Morse et al. | |
| 5,655,546 | A | | 8/1997 | Halpern | |
| 5,817,098 | A | * | 10/1998 | Albrektsson et al. ...... | 606/96 |
| 5,885,293 | A | * | 3/1999 | McDevitt ............ | 606/80 |
| 5,904,717 | A | | 5/1999 | Brekke et al. | |
| 5,919,196 | A | | 7/1999 | Bobic et al. | |
| 6,007,496 | A | | 12/1999 | Brannon | |
| 6,110,178 | A | | 8/2000 | Zech et al. | |
| 6,146,385 | A | | 11/2000 | Torrie et al. | |
| 6,179,871 | B1 | | 1/2001 | Halpern | |
| 6,187,329 | B1 | | 2/2001 | Agrawal et al. | |

(Continued)

OTHER PUBLICATIONS

Malinin et al., "Hypothermic Storage and Cryopreservation of Cartilage," *Clinical Orthopedics and Related Research*, No. 197, pp. 15-26 (Jul.-Aug. 1985).

(Continued)

*Primary Examiner*—Corrine McDermott
*Assistant Examiner*—Javier G. Blanco
(74) *Attorney, Agent, or Firm*—Harness, Dickey & Pierce, P.L.C.

(57) ABSTRACT

Provided are procedures and instruments for preparing and transplanting osteochondral allograft plugs to a host bone to repair an articular cartilage defect. An allograft bone plug having a cartilage plate and cancellous bone tissue attached thereto is removed from a donor bone. The allograft plug is further shaped by removing or cutting away cancellous bone tissue to form a cancellous stalk extending from the cartilage plate. The formed cancellous stalk can have any suitable shape including cylindrical, conical, and rectilinear. At the recipient site of the host bone, a cutout is formed corresponding in shape to the allograft plug. The allograft plug is inserted into the cutout such that the cancellous stalk is retained in the host bone and the cartilage plate aligns with the condyle surface of the host bone. Aspects of the invention may also be applicable to preparing and transplanting osteochondral autograft plugs.

12 Claims, 12 Drawing Sheets

U.S. PATENT DOCUMENTS

| | | | |
|---|---|---|---|
| 6,242,247 | B1 | 6/2001 | Rieser et al. |
| 6,358,253 | B1 | 3/2002 | Torrie et al. |
| 6,375,658 | B1 | 4/2002 | Hangody et al. |
| 6,387,693 | B2 | 5/2002 | Rieser et al. |
| 6,395,011 | B1 | 5/2002 | Johanson et al. |
| 6,488,033 | B1 | 12/2002 | Cerundolo |
| 6,528,052 | B1 | 3/2003 | Smith et al. |
| 6,530,928 | B1 | 3/2003 | Frei et al. |
| 6,591,581 | B2 | 7/2003 | Schmieding |
| 6,592,588 | B1 | 7/2003 | Bobic et al. |
| 6,613,054 | B2 | 9/2003 | Scribner et al. |
| 6,727,224 | B1 | 4/2004 | Zhang et al. |
| 6,740,484 | B1 | 5/2004 | Khirabadi et al. |
| 6,835,377 | B2 | 12/2004 | Goldberg et al. |
| 6,852,114 | B2 | 2/2005 | Cerundolo |
| 2002/0082704 | A1* | 6/2002 | Cerundolo ............... 623/20.35 |
| 2003/0009218 | A1* | 1/2003 | Boucher et al. ......... 623/13.14 |
| 2004/0230303 | A1 | 11/2004 | Gomes et al. |

OTHER PUBLICATIONS

Malinin et al., "Articular Cartilage Nutrition is Mediated by Subchondral Bone: a Long-Term Autograft Study in Baboons," *Osteoarthritis and Cartilage*, vol. 8, pp. 483-491, OsteoArthritis Research Society Intl. (2000).

Convery et al., "Long-Term Survival of Chondrocytes in an Osteochondral Articular Cartilage Allograft," *Journal of Bone and Joint Surgery*, vol. 78-A, No. 7, pp. 1082-1088 (Jul. 1996).

Williams et al., "Prolonged Storage Effects on the Articular Cartilage of Fresh Human Osteochondral Allografts," *Journal of Bone and Joint Surgery*, vol. 85-A, No. 11, pp. 2111-2120 (Nov. 2003).

Hangody et al., "Autologous Osteochondral Mosaicplasty for the Treatment of Full-Thickness Defects of Weight-Bearing Joints," *Journal of Bone and Joint Surgery*, vol. 85-a, Supp. 2, pp. 25-32 (2003).

Chu et al., "Articular Cartilage Transplantation—Clinical Results in the Knee," *Clinical Orthopaedics and Related Research*, No. 360, pp. 159-168 Lippincott, Williams & Wilkins, (Mar. 1999).

Hangody et al., "Autologous Osteochondral Mosaicplasty for the Treatment of Full-Thickness Defects of Weight-Bearing Joints," *Journal of Bone and Joint Surgery*, vol. 85-a, Supp. 2, pp. 25-32 (2003) *Note: this is a resubmission of reference No. BA, previously submitted on Feb. 6, 2006.*

* cited by examiner

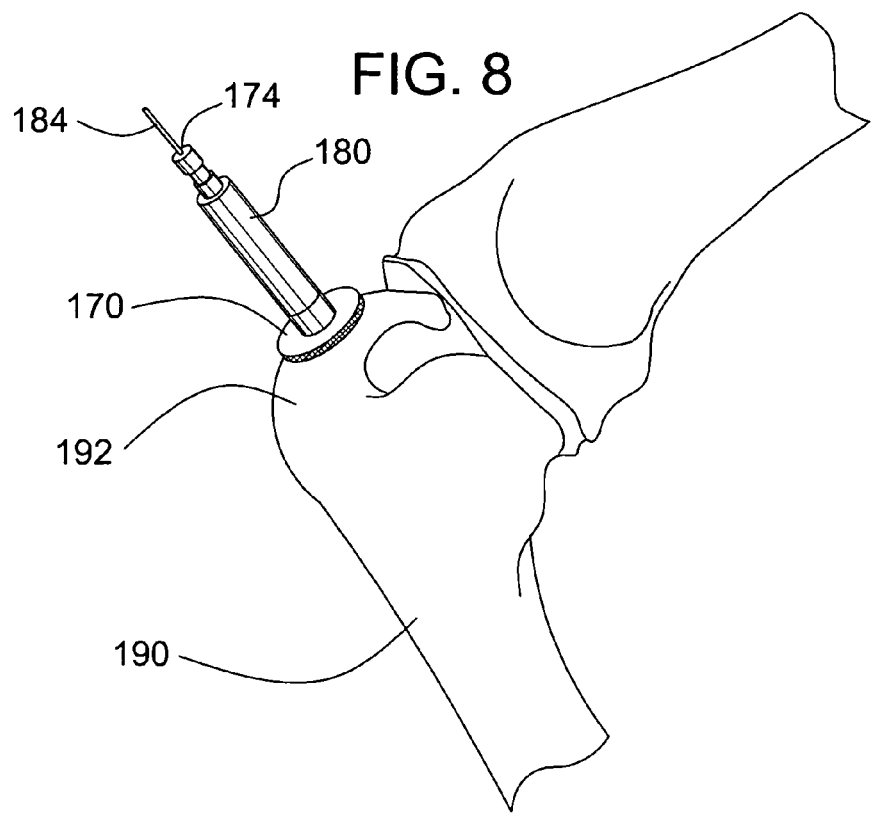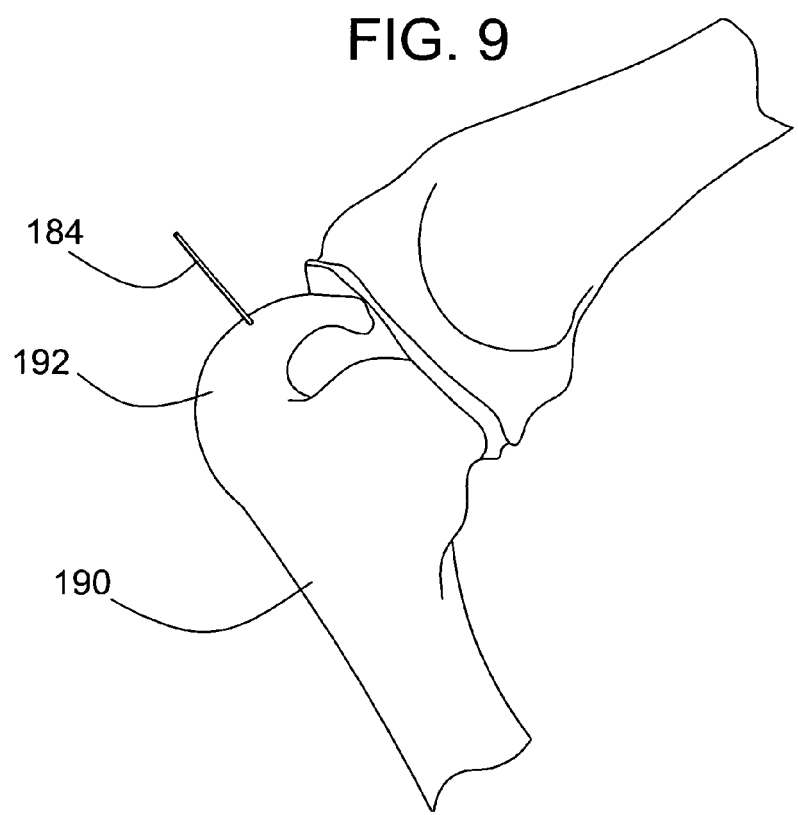

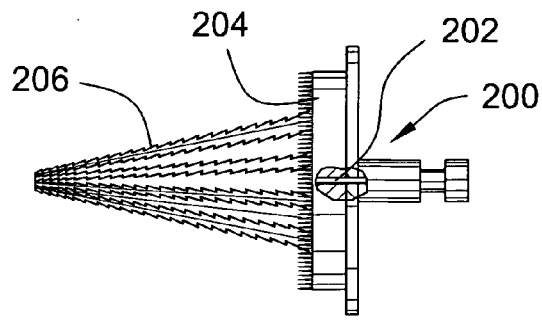
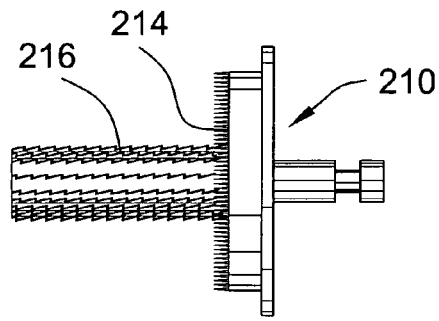
FIG. 10
FIG. 11
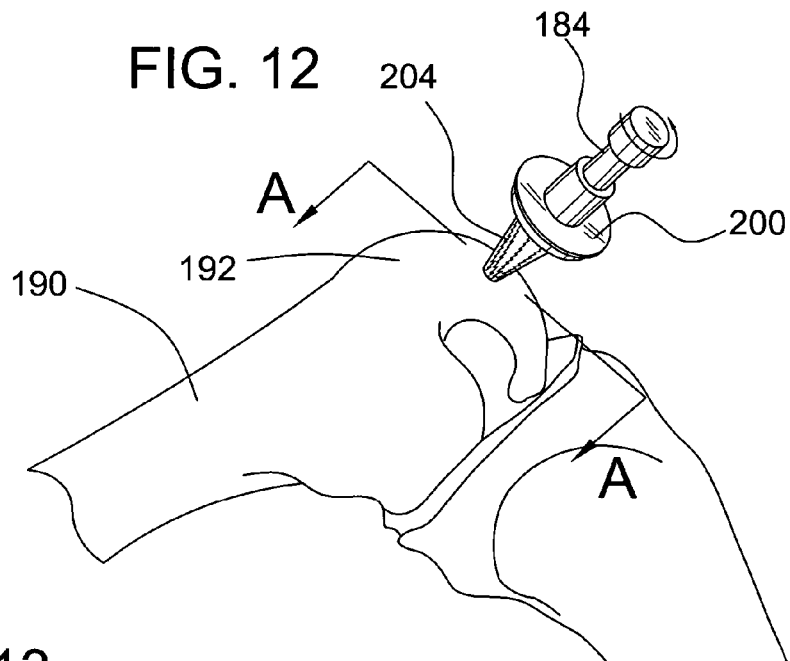
FIG. 12
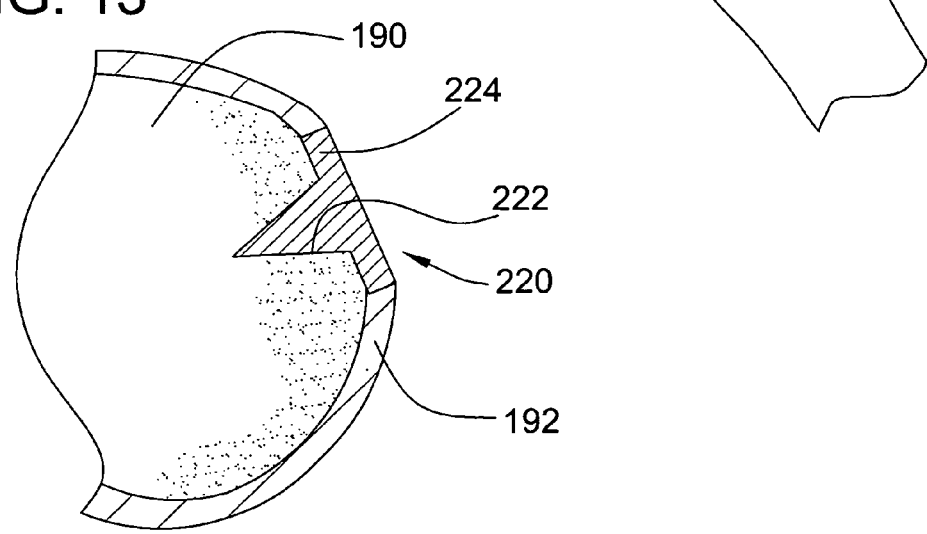
FIG. 13

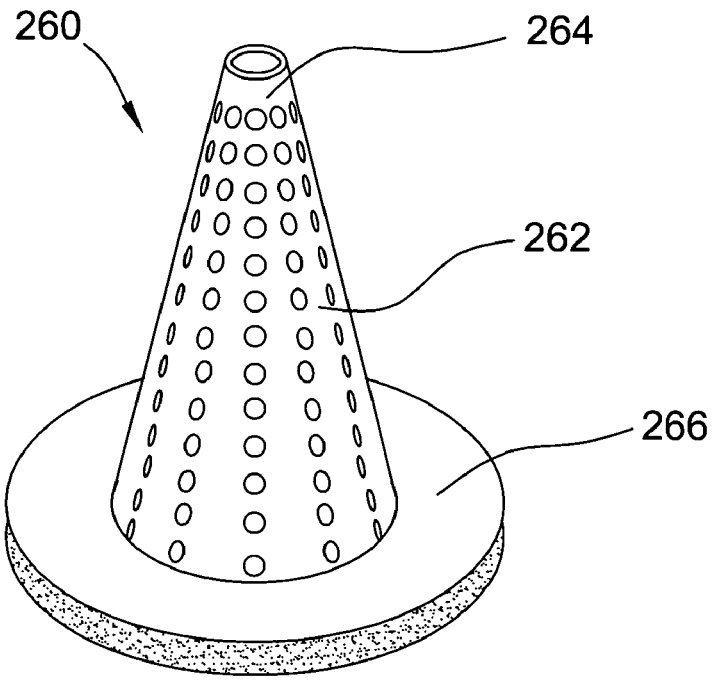
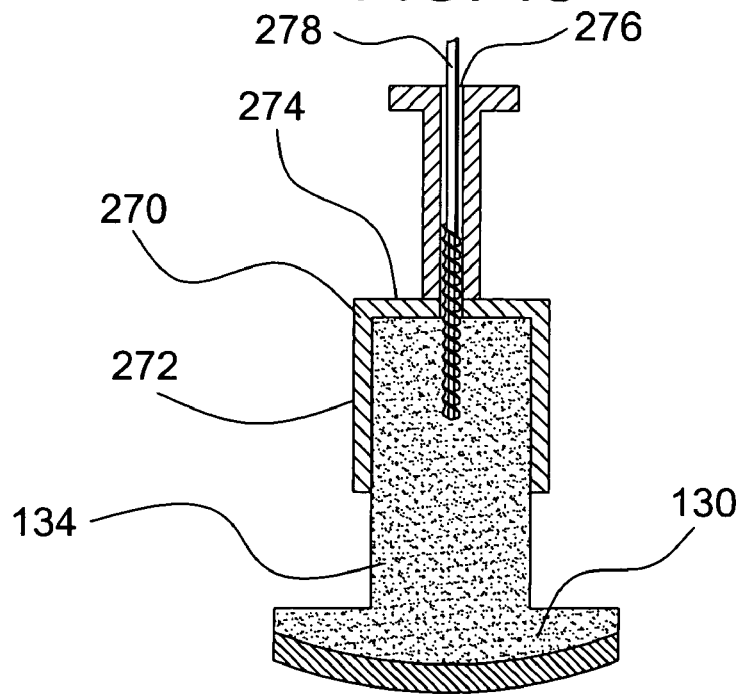

METHOD AND INSTRUMENTATION FOR THE PREPARATION AND TRANSPLANTATION OF OSTEOCHONDRAL ALLOGRAFTS

BACKGROUND OF THE INVENTION

In humans and many other animals, cartilage is present on the surface of bones that form articular joints to facilitate articulation of the joint and protect and cushion the bones. However, defects may develop in the cartilage from various causes such as abrupt trauma or prolonged wear. A number of techniques have been attempted to treat such cartilage defects. One such technique is the transplantation of fresh osteochondral allografts.

In this procedure, an allograft plug, also known as a osteochondral plug or core, is harvested from a condyle or rounded joint-forming portion of a donor bone. Intact on the surface of the allograft plug, on a portion of the bone known as the cartilage plate, is healthy cartilage. The allograft plug may also have attached to the cartilage plate cancellous tissue, which is the porous inner material that is present in many bones. In the recipient patient, the cartilage defect and the corresponding portion of 2 bone are cutaway and removed from the joint. The allograft plug is then inserted and attached to the cutaway portion so that the cartilage plate and healthy cartilage of the allograft plug align with the cartilage on the surface of the host bone.

One problem that arises with osteochondral allografts is that the recipient may adversely respond or reject the allograft plug. This can happen primarily because of the antigenic material contained in the cancellous bone of the allograft plug. Occurrence of such an adverse response may result in the recipient site reforming or healing in such a manner that the allograft plug becomes walled off from the host bone thereby delaying or preventing incorporation of the allograft. In addition, physically attaching and securing the allograft plug to the recipient site presents difficulties.

BRIEF SUMMARY OF THE INVENTION

The invention provides methods and instruments for preparing and transplanting osteochondral allografts to repair articular cartilage defects. According to one aspect of the invention, an allograft plug having a cartilage plate and cancellous bone tissue attached thereto is removed from a donor bone. The allograft plug is further shaped by removing or cutting away cancellous bone tissue to form a cancellous stalk extending from the cartilage plate. The formed cancellous stalk can have any suitable shape including cylindrical, conical, and rectilinear. According to another aspect of the invention, in what will become the host bone of the patient, a recipient site is prepared by forming a cutout corresponding to the cartilage defect. The shape of the cutout generally corresponds to the shape of a provided allograft plug from which cancellous material has been removed to form a cancellous stalk. The allograft plug is inserted into the cutout such that the cancellous stalk is retained in the host bone and the cartilage plate aligns with the condyle surface of the host bone. Removing and shaping the allograft plug can be performed separately or together with preparing a recipient site by forming a cutout and inserting the allograft plug into the cutout.

To prepare the recipient site, a template can be attached to the host bone in a location corresponding to the cartilage defect. In an aspect of the invention, the template can include a guide aperture disposed therein. To facilitate alignment of subsequent operations, an elongated guide pin is inserted through the guide aperture and into the host bone. Cannulated drill bits having the desired shape can be slid over the guide pin and driven into the host bone to form the shaped cutout. In another aspect of the invention, the template can include a plurality of cut slots disposed therein. A cutting device can then be inserted through the cut slots and into the host bone to form the shaped cutout.

To remove and shape the allograft plug from the donor site, a second template specially adapted to attach to the donor bone can be used. One advantage of employing a template to remove the allograft plug is that template may facilitate simultaneous shaping of the allograft plug at the time of removal. In other embodiments, the allograft plug can initially be a piece of cylindrically or otherwise shaped bone material removed from the donor bone and subsequently shaped to produce the finished allograft plug.

It should be recognized that various aspects of the invention may also be applicable to preparing and transplanting an osteochondral autograft plug, a process which involves removing a plug from a first location and transplanting the plug into a second location within the same patient.

The invention provides one or more of the following advantages: An advantage of the invention is that it provides a osteochondral allograft plug that has a reduced amount of cancellous tissue and is therefore less likely to be rejected by a recipient. Another advantage is that it provides a specially shaped osteochondral allograft plug that can be fit and anchored into a correspondingly shaped cutout at the recipient site. These and other advantages and features of the invention will be apparent from the detailed description and the accompanying drawings.

BRIEF DESCRIPTION OF THE SEVERAL VIEWS OF THE DRAWINGS

FIG. 8 is a perspective view of the template of FIG. 6 attached to the condyle of host bone in accordance with an embodiment of the invention, the handle being engaged to the template and a guide pin being inserted through the template FIG. 9 is a perspective view of the guide pin inserted into the condyle of the host bone after removal of the template.

FIG. 10 is a side elevational view of another embodiment of a cannulated drill bit for forming a cutout in a recipient site in accordance with an embodiment of the invention, the drill bit having a counter-bore forming element and a conical cutting body with a central cannula shown in cutaway.

FIG. 11 is a side elevational view of another cannulated drill bit for forming a cutout in a recipient site in accordance with an embodiment of the invention, the drill bit having a counter-bore forming element and a cylindrical cutting body.

FIG. 12 is a perspective view of the drill bit of FIG. 9 being driven into the condyle of the host bone to form the cutout.

FIG. 13 is a cross-sectional view taken generally along line A-A of FIG. 12 illustrating cutout formed into a recipient site of a condyle of a host bone.

FIG. 17 is a top perspective view of a cannulated burring shell for removing cancellous material and shaping a conically shaped allograft plug.

FIG. 18 is a cross-sectional view of a sleeve placed about an allograft plug having a cylindrical shaped cancellous stalk and a guide pin inserted through the sleeve and partially into the cancellous stalk.

DETAILED DESCRIPTION OF THE INVENTION

Figure 1:
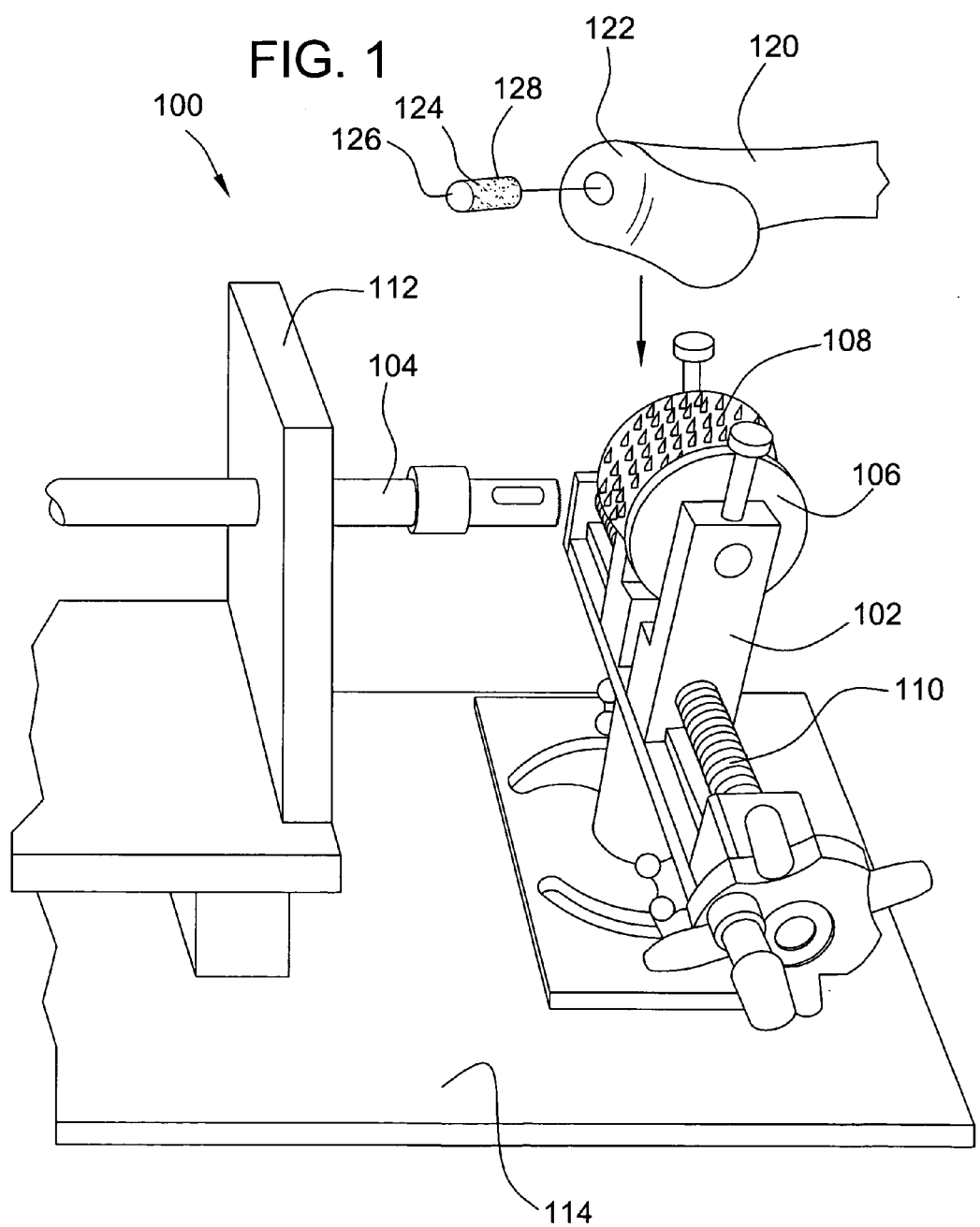
FIG. 1 is a perspective view of a device for removing from a donor bone a transplantable osteochondral allograft plug for repairing a cartilage defect.

Now referring to the drawings, wherein like reference numbers refer to like elements, there is illustrated various processes and instruments for preparing and transplanting an osteochondral allograft in accordance with the various embodiments of the invention. Referring first to FIG. 1, there is shown a device 100 suitable for cutting and forming a cylindrically shaped allograft plug 124 from a donor bone 120 in accordance with one aspect of the invention. The device 100 itself includes a clamp assembly 102 and a tubular crown saw 104. The clamp assembly 102 includes two vertically extending clamp pads 106, 108, that can be moved with respect to each other by rotation of a linear screw mechanism 110. The crown saw 104 is directed towards and linearly movable with respect to the clamp assembly 102. To align the clamp assembly 102 and crown saw 104, the crown saw can pass through a vertical alignment plate 112 joined to a base 114 onto which the clamp assembly is also mounted.

To produce an allograft plug, a donor bone 120 or a portion thereof having on its surface healthy cartilage is received between the clamp pads 106, 108 and the clamp pads are moved together to grasp and hold the donor bone in alignment with the crown saw 104. Preferably, the donor bone 120 can be received in the clamp assembly 102 such that a condyle 122 corresponding to a donor site on the donor bone 120 is positioned towards the crown saw 104. The rotating tubular crown saw 104 is moved towards and into the donor site 122 to form a cylindrical cut into the donor bone 120, after which the crown saw can be removed. The cylindrically shaped bone material 124 produced by the cylindrical cut and that will correspond to the allograft plug can then be removed from the remainder of the donor bone 120 by, for example, transecting the donor bone with a saw or by propagating a crack through the donor bone with a tamp or similar device.

The removed cylindrical shaped bone material 124 has a cartilage plate 126 corresponding to the outer surface of the donor bone 120 and on which healthy cartilage is located. Extending from the cartilage plate 126 is cancellous bone tissue 128 from the interior portion of the donor bone 120. As will be appreciated by those of skill in the art, when making the cut into the donor site 122, the donor bone 120 and the crown saw 104 are preferably arranged so that the contour of the cartilage plate 126 corresponds to the portion of the host bone which is to be repaired.

Once the cylindrically cut bone material has been removed, it can be shaped by any variously suitable subsequent shaping operation to remove cancellous bone tissue and form a cancellous stalk extending from the cartilage plate. Removing cancellous bone tissue results in the cancellous stalk having a reduced cross section compared to the cross-section of the cartilage plate.

Because the cancellous bone tissue on the allograft plug could contain antigenic material, reducing the amount of cancellous bone tissue transplanted to the host reduces the possibility of an adverse reaction within the host. Another advantage of shaping the allograft plug to form a cancellous stalk is that the stalk provides an anchor-like structure that assists in anchoring the allograft plug into a recipient site on the host bone. A related advantage is that, by removing cancellous tissue from the cancellous stalk, the amount of cancellous tissue that must be accommodated by the host bone during transplantation is reduced. Accordingly, the size of the cutout that must be formed into a recipient site on the host bone is likewise reduced thereby requiring less trauma to the host bone.

The finished allograft plug can have any suitable shape. For example, referring to FIG. 2, there is illustrated an allograft plug 130 having a circular cartilage plate 132 and a cylindrical cancellous stalk 134 of cancellous bone tissue extending therefrom. The cartilage plate 132 has a generally circular perimeter of a first diameter and includes healthy cartilage from the donor intact on subchondral bone tissue 136. On the underside of the cartilage plate 132 there may also be a thin layer of cancellous bone tissue 138 which corresponds to the first diameter. The cylindrically shaped cancellous stalk 134 extends from the thin layer of cancellous bone tissue 138 and has a second perimeter or second diameter reduced in size with respect to the first diameter. The reduction in size of the second perimeter compared to the first perimeter is the result of removing cancellous bone tissue to form the stalk. Preferably, the circular cartilage plate 132 and the cylindrical cancellous stalk 134 are coaxial.

Figure 3:
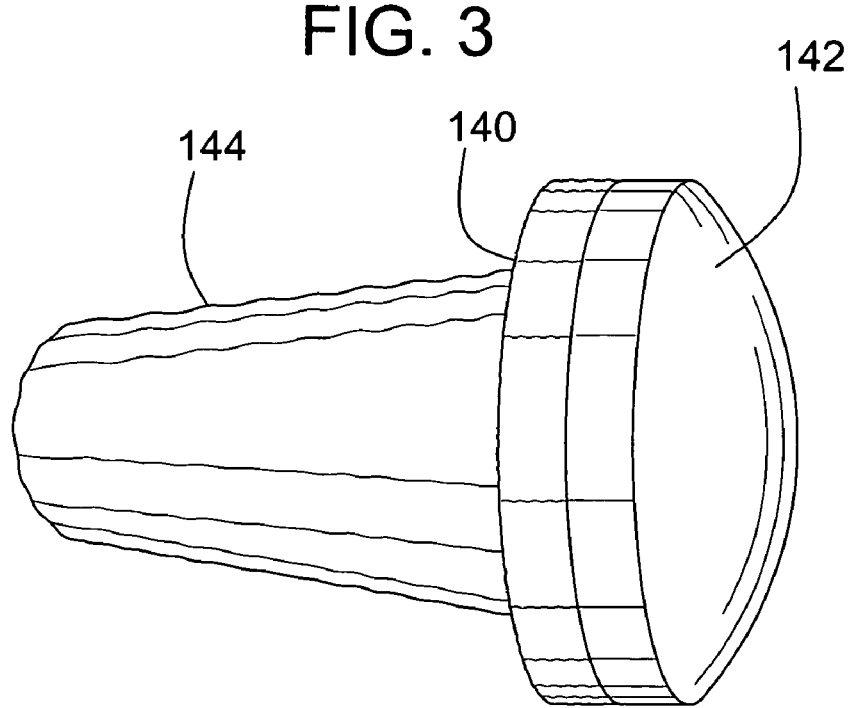
FIG. 3 is a perspective view of another embodiment of an allograft plug having a cartilage plate and a conical cancellous stalk.

Referring to FIG. 3, there is illustrated another embodiment of an allograft plug 140 having circular cartilage plate 142 and a generally conical cancellous stalk 144 extending therefrom. The cartilage plate 142 again has a first perimeter of a given first diameter while the concial perimeter of the cancellous stalk tapers so as to progressively reduce in diameter as the stalk extends from the cartilage plate. Preferably, the circular cartilage plate 142 and the conical cancellous stalk are coaxial. In other embodiments, the cancellous stalk may have a stepped shape with each step having a reduced perimeter or diameter compared to the first perimeter of the cartilage plate.

Figure 4:
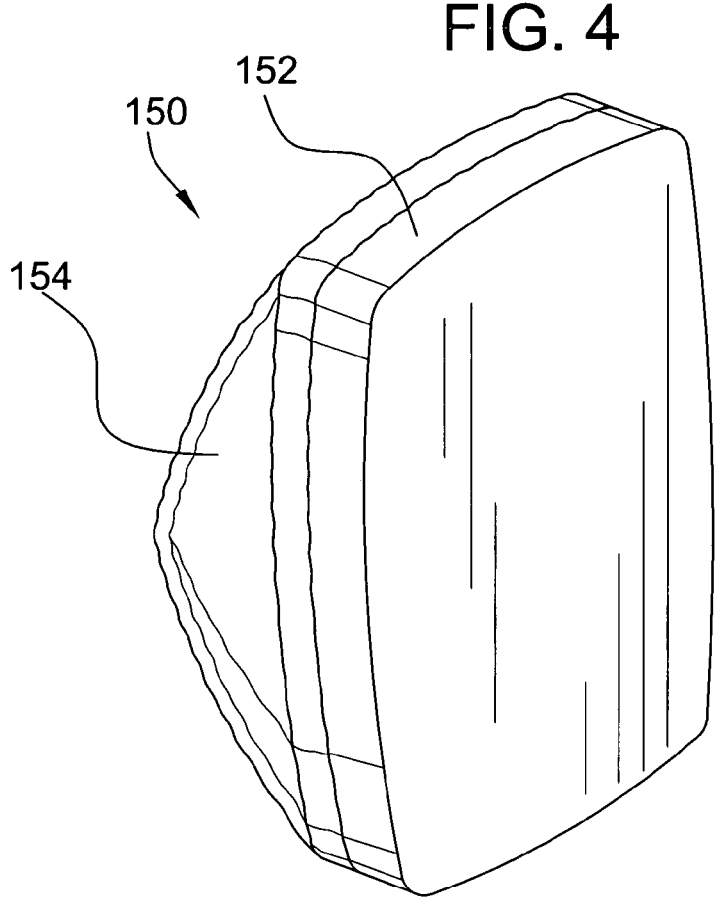
FIG. 4 is a perspective view of another embodiment of an allograft plug having a rectangular shape.
Figure 5:
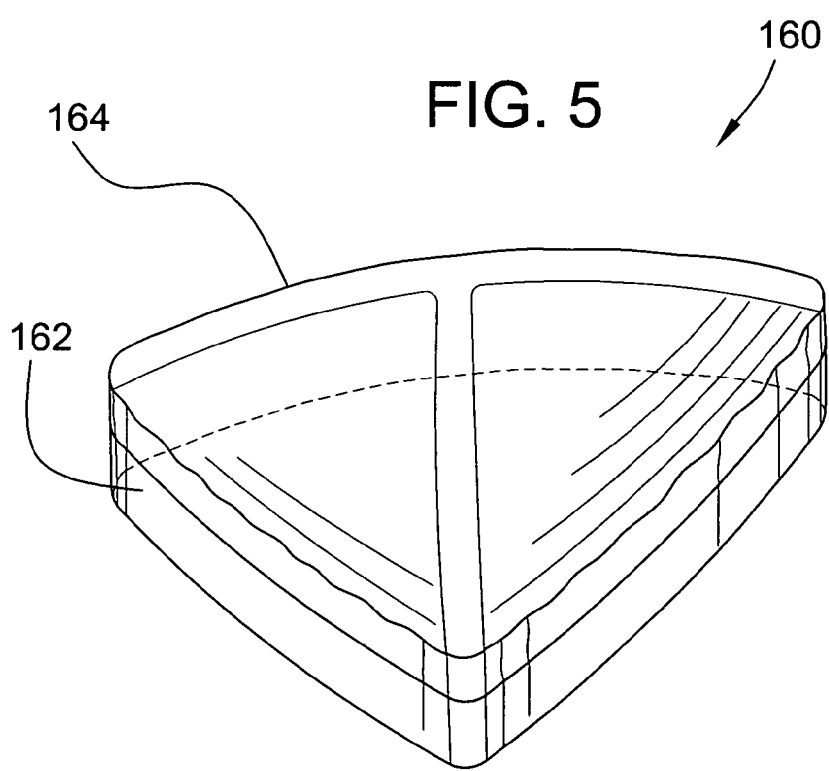
FIG. 5 is a perspective view of another embodiment of an allograft plug having a triangular shape.

Referring to FIG. 4, there is illustrated another embodiment of an allograft plug 150 having rectangular cartilage plate 152 with a tapering or rectangular pyramid-shaped cancellous stalk 154. As will be appreciated, the tapering of the cancellous stalk 154 results in a progressive reduction of its cross-section with respect to the cross-section of the rectangular cartilage plate 152. Referring to FIG. 5, there is illustrated an allograft plug 160 having a triangular cartilage plate 162 and a tapering triangular pyramid-shaped cancellous stalk 164 extending therefrom. In other embodiments, the rectangular and triangular cartilage plates can have respective rectangular and triangular cross-sectioned stalks extending therefrom.

Figure 6:
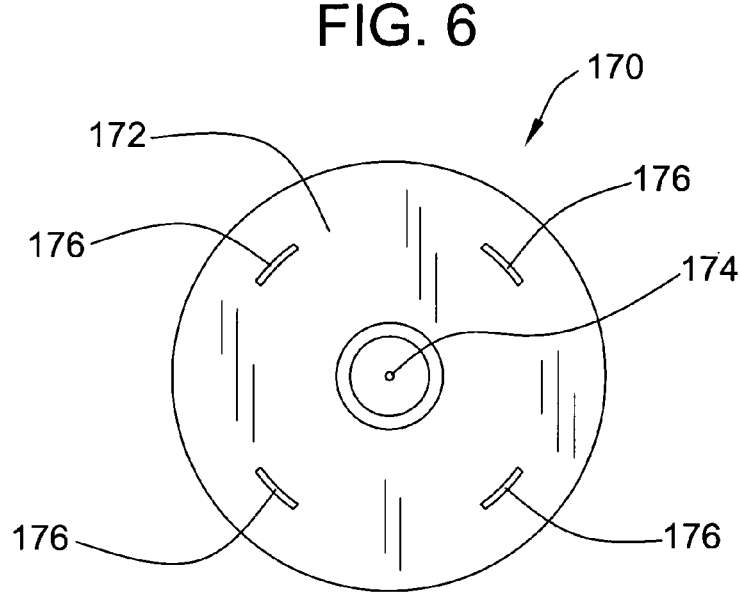
FIG. 6 is a front elevational view of a template for preparing a recipient site in accordance with the teachings of the invention, the template including a central guide aperture.
Figure 7:
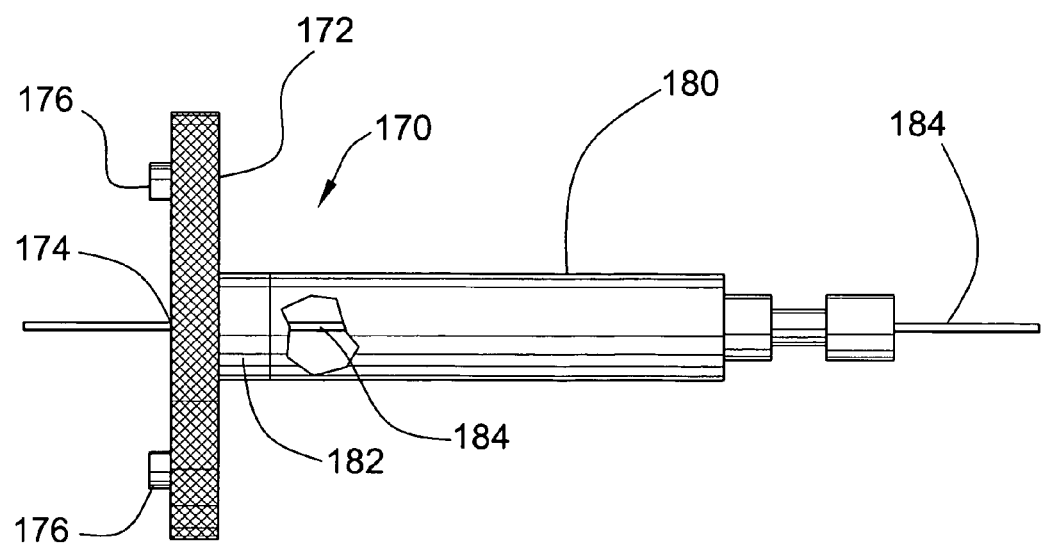
FIG. 7 is a side elevational view of the template shown in FIG. 6 and further illustrating a detachable handle engaged to the template.

To prepare a recipient site in a host bone for receiving the allograft plug, special instruments can be used to form a cutout corresponding in shape to the allograft plug. Such special tools can include, for example, a template 170 as illustrated in FIGS. 6 and 7. The template 170 includes a flat, circular template plate 172 through the center of which is disposed a guide aperture 174. From one surface of the template plate 172 there projects a short distance a plurality of sharp teeth 176. The teeth 176 are preferably arranged in a circular pattern concentric with the circular template plate 172. To enable manipulation of the template 170, the template preferably also includes a detachable handle 180 that engages a corresponding engagement structure 182 on the opposite surface of the plate 172 from which the teeth 176 project. The handle 180 and plate 172 can be engaged by, for example, a twist lock mechanism. In various embodiments, the guide aperture 174 can continue through the detachable handle 180 as well. The guide aperture 174 is adapted to receive a guide pin 184 in a sliding fit such that the guide pin 184 can be inserted through the center of the plate 172.

When preparing a recipient site with the template, referring to FIG. 8, a joint such as a knee joint of the patient being treated is first manipulated to expose the cartilage defect on the surface of a condyle 192 of a host bone 190. Once the cartilage defect is suitably exposed, the template 170 is attached via the sharp, projecting teeth to the condyle 192 at a location corresponding to the defect. Preferably, to minimize damage, the circular pattern of the teeth projecting from the template corresponds to the area of the defect. Once the template 170 is attached, the detachable handle 180 can be removed and the guide pin 184 inserted through the guide aperture 174 and into the host bone 190 at the location of the defect. Once the guide pin 184 is driven into the host bone 190, the handle 180 can be reattached to the template 170 and the template pull over the guide pin and removed from the condyle 192. In other embodiments, the guide pin can be inserted with the handle remaining attached to the template. Thereafter, the guide pin 184 remains inserted into the condyle 192 as illustrated in FIG. 9.

To form the cutout that removes the cartilage defect and receives the shaped allograft plug, a shaped drill bit, burr, or cutting disc can be employed. The shape and dimensions of the drill bit, burr or cutting disc, which will determine the shape and dimension of the formed cutout, may correspond to the allograft that is to be transplanted. An embodiment of such a drill bit 200 is illustrated in FIG. 10. Disposed along the central axis of the drill bit 200 is a tube or cannula 202 adapted to receive the guide pin. The drill bit 200 also includes a circular counter-bore forming element 204 and a conical-shaped cutting body 206 extending from the counter-bore forming element. The surface of the counter-bore forming element 204 and the cutting body 206 can include flutes or other suitable cutting structures. In other embodiments, to produce differently shaped cutouts, a different drill bit, burr, or cutting disc can be utilized. For example, referring to FIG. 11, there is illustrated a cannulated drill bit 210 having a circular counter-bore forming element 214 and a cylindrical cutting body 216.

In use, referring to FIG. 12, the conically cannulated drill bit 200 (or burr or cutting disc when used) is slid onto the guide pin 184 and placed proximate the host bone 190 such that the cutting body 204 is proximate the cartilage defect. The drill bit 200 can be rotated as indicated, either by hand or by a powered device, to cut into and remove the cartilage defect and the associated bone material thereby forming the cutout. Where desirable, lubrication can be supplied to facilitate cutting. Referring to FIG. 13, the shape of the cutout 220 formed into the host bone 190 will correspond to the shape of the drill bit used including having a conical void 222 and a circular counter bore 224 proximate the surface of the condyle 192. As will be appreciated, when the cannulated drill bit 210 illustrated in FIG. 11 is used, the formed cutout will have a corresponding shape including a circular counter-bore and a cylindrical void. In various embodiments, the shaped drill bits, burrs, and cutting disc can be used to make finishing cuts with different devices used to make initial cuts into the recipient site.

Figure 14:
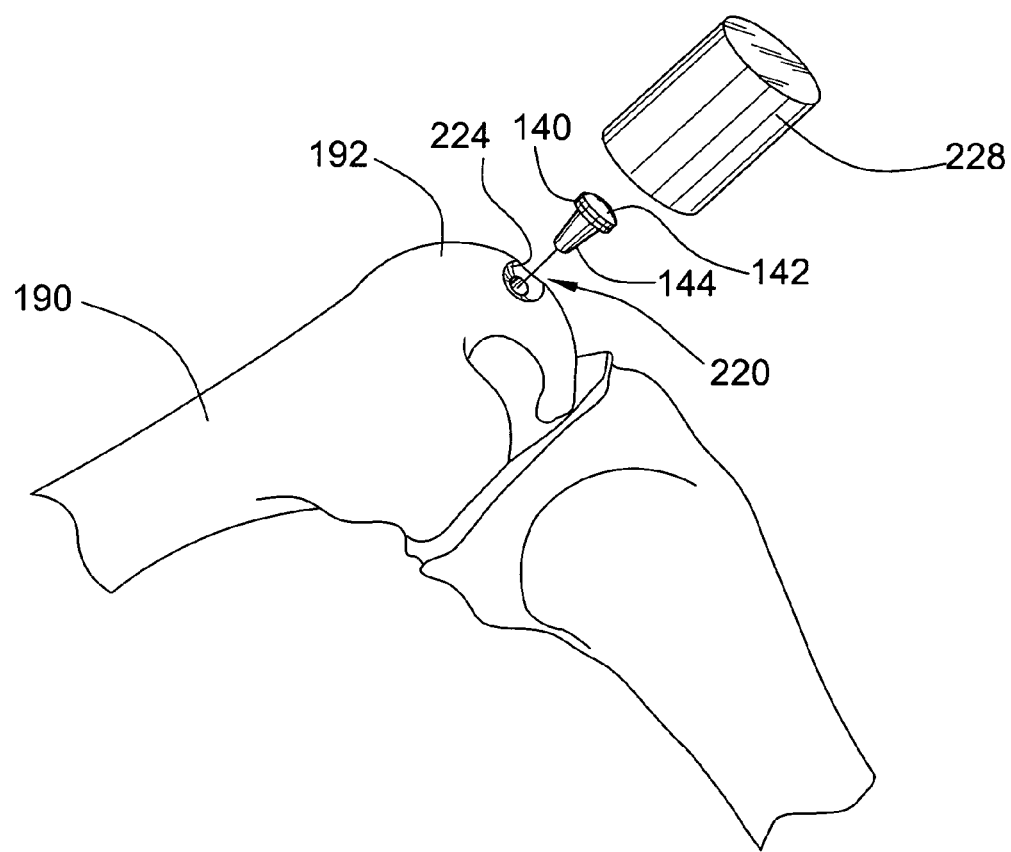
FIG. 14 is a perspective view of the condyle of a host bone illustrating a method of inserting an shaped allograft plug into a cutout formed at a recipient site using a tamp.

Referring to FIG. 14, a correspondingly shaped conical allograft plug 140 can be inserted into the shaped cutout 220 at the recipient site using a tamp 228 if necessary. Preferably, the allograft plug 140 and cutout 220 are sized to provide a close fit and, more preferably, a slight press fit, when engaged. Once properly inserted, the shaped cancellous stalk 144 is received deep into the cutout 220 and thus functions to anchor the allograft plug 140 to the host bone 190. Additionally, the cartilage plate 142 will be accommodated in the counter bore 224 such that the healthy cartilage of the allograft plug 140 aligns with the healthy cartilage on condyle 192 of the host bone 190. Overtime, the cancellous tissue and cartilage plate will permanently graft with the healthy bone tissue.

Figure 15:
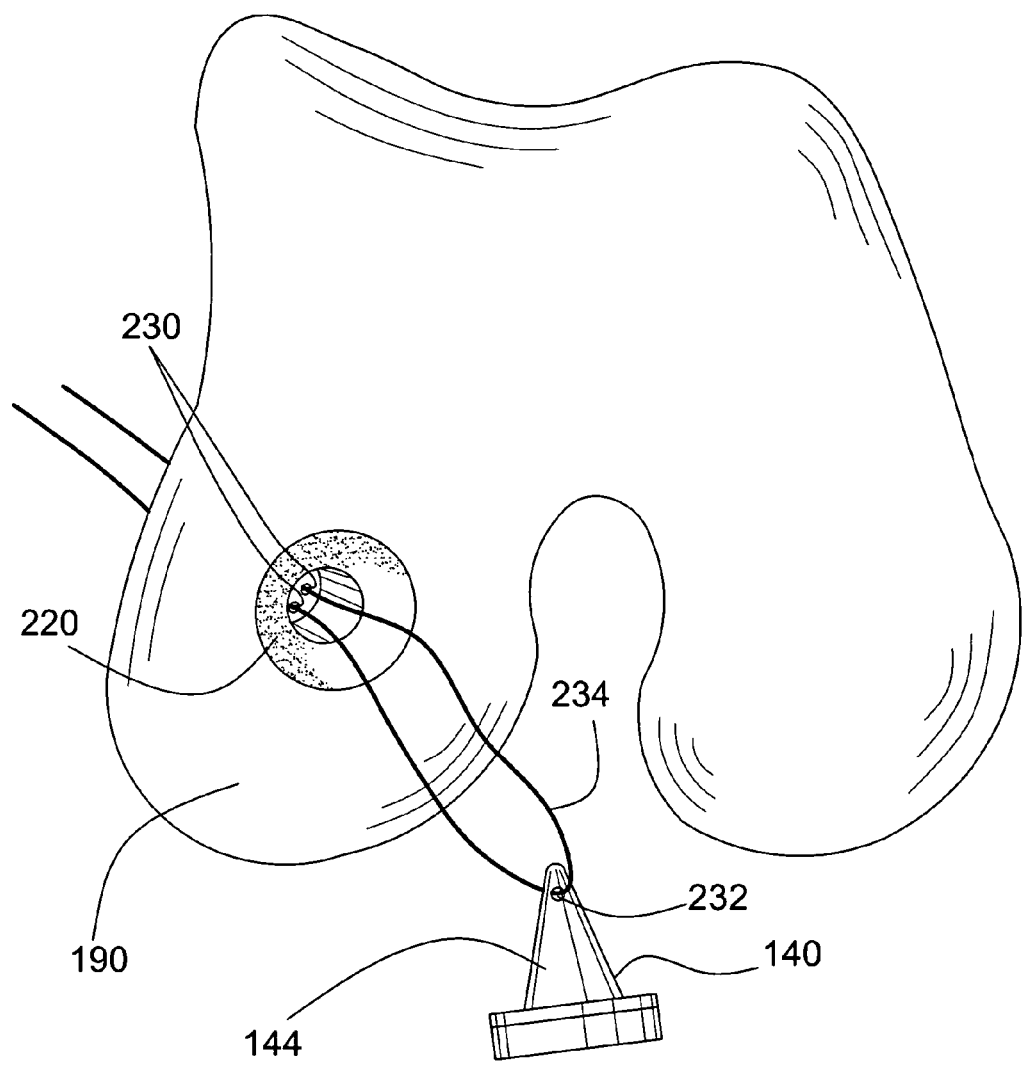
FIG. 15 is a front elevational view of the condyle of a host bone illustrating another method of inserting a shaped allograft plug into a cutout formed at a recipient site using a suture.

While inserting the allograft with a tamp is a common method, any other suitable method can be employed. For example, referring to FIG. 15, a method of implanting a conically shaped allograft plug 140 by the use of sutures is illustrated. According to the method, a pair of parallel holes 230 are cut into the outline of the cutout 220 and through to the opposite side of the host bone 190. A third hole 232 is cut transversely across the cancellous stalk 144 of the conical allograft plug 140. A flexible suture 234 or line can be run through the hole 232 in the cancellous stalk 144 with the ends of the suture run through holes 230 in the cutout 220 and out the opposite side of the host bone 190. As will be appreciated, pulling the ends of the suture 234 through holes 230 will draw the allograft plug 140 tightly into the cutout 220. It will be appreciated that any of the foregoing implantation procedures can work for any of the various shaped allograft plugs and corresponding cutouts.

Preparing the recipient site and removing and shaping an allograft plug for transplanting into the recipient site can occur simultaneously or, in some embodiments, the allograft plug can be removed and shaped in advance of preparing the recipient site. Moreover, the preparation of an allograft plug can occur at a different location than the where the insertion of the allograft plug is to occur. To preserve an allograft plug prior to insertion, the allograft plug can be cryogenically preserved. This is an alternative to preparing and transplanting a fresh allograft plug.

Figure 16:
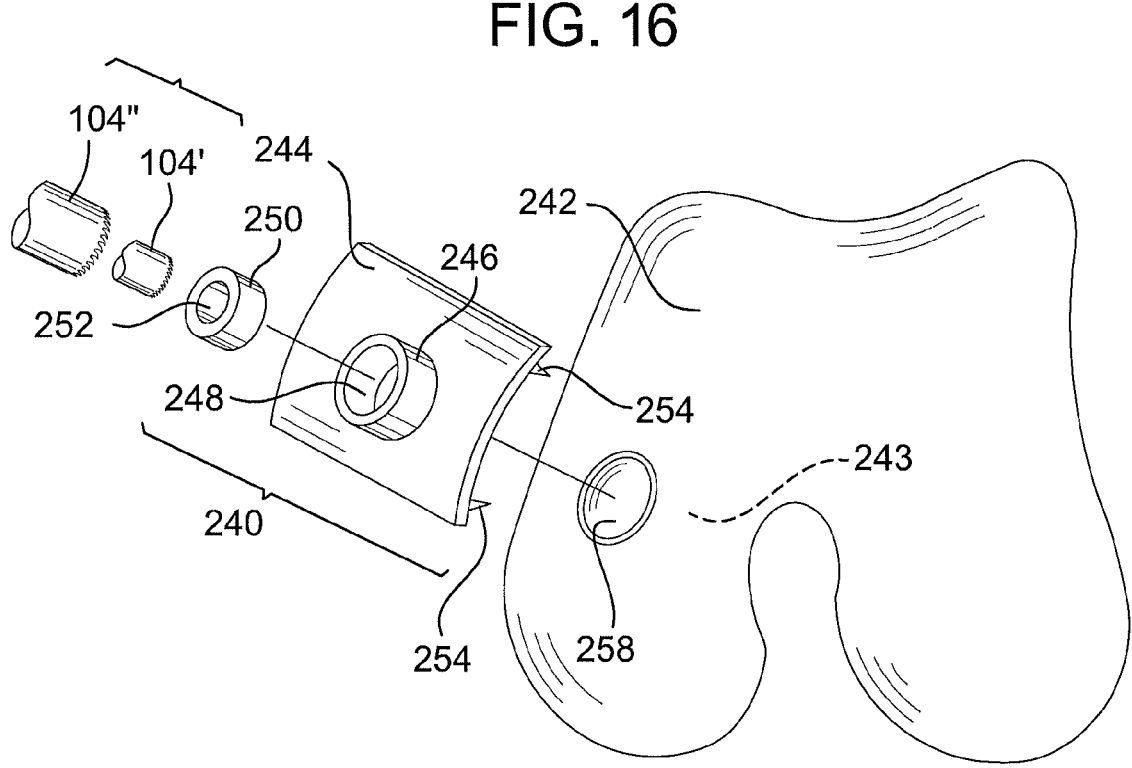
FIG. 16 is a perspective view of a guide plate with a removable guide cylinder for assisting in removing and shaping a cylindrically shaped allograft plug from a donor bone.

Though the foregoing procedures for preparing and transplanting a shaped allograft plug can be conducted with any common medical instruments, in a further aspect of the invention, various special instruments and tools, in addition to the template and the shaped drill bit, burr, or cutting discs, are provided. For example, to produce the shaped allograft plug illustrated in FIG. 2 from a donor bone, a guide plate 240 as illustrated in FIG. 16 can be used to guide various crown saw cuts into a donor bone 242. The guide plate includes a generally rectangular base plate 244 that is curved or cambered to fit on a condyle of the donor bone and from one surface of which projects a circular guide cylinder 246. The guide cylinder 246 defines a hollow bore 248 of a first diameter that is disposed through the base plate 244. Slidably receivable in the guide cylinder 246 is a smaller second guide cylinder 250 through which is disposed a second hollow bore 252 of a second, smaller diameter. The guide plate 240 also includes a plurality of short sharp teeth 254 projecting from a surface of the base plate 244 opposite the guide cylinder 246.

Figure 2:
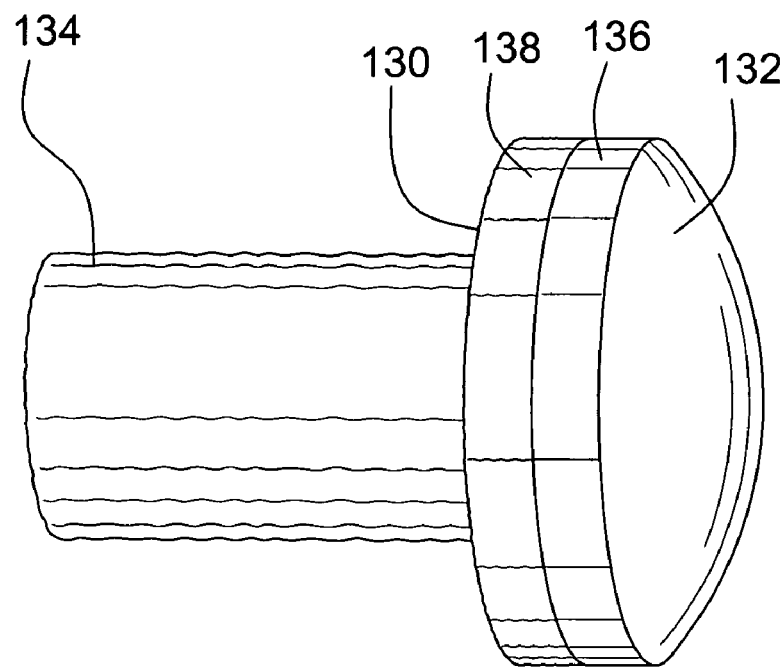
FIG. 2 is a perspective view of an allograft plug shaped in accordance with an embodiment of the invention, the allograft plug having a cartilage plate and a cylindrical cancellous stalk.

In use, the guide plate 240 with the second guide cylinder 250 inserted is attached to the donor bone 242 on a surface diametrically opposite of the donor site 243. The teeth 254 help attach the guide plate to the donor bone 242 and can be inserted into the donor bone by thumb pressure or a light tamp. To produce a first cut into the donor bone 242, a tubular crown saw 104' having a diameter slightly less than diameter of the second hollow bore 252 of the guide plate 240 is inserted through the second hollow bore and into the donor bone. Preferably, the first cut is made into the donor bone 242 from the location of the guide plate 240 opposite the donor site 243 to a point proximate the cartilage plate of the donor site and more preferably only a few millimeters from the cartilage plate. The second, smaller guide cylinder 250 is then removed from the guide plate 240. A second crown saw 104", larger than the first crown saw 104' but with a diameter adapted to be slidably received into the first hollow bore 248 of the guide plate 240, is inserted through the first hollow bore and across the donor bone 242, thereby detaching a portion of bone tissue 258 from the donor bone. The detached bone tissue can then be trimmed to a desired length, for example, as measured from the cartilage plate to the cancellous tissue, to produce the allograft plug 130 having the cylindrical cancellous stalk 134 as illustrated in FIG. 2. Hence, the guide plate helps avoid injury to adjacent normal cartilage on the donor bone. Furthermore, the guide plate 240 can be used in conjunction with a clamping device of the type illustrated and described with respect to FIG. 1. In other embodiments, the guide plate 240 can be used with only the first guide cylinder 246 and the second, larger diameter crown saw 104" to produce a cylindrical allograft plug that can be subsequently shaped.

To produce an allograft plug having a conical shaped cancellous stalk, as illustrated in FIG. 3, a cannulated burring shell can be used in conjunction with a specially adapted sleeve to further remove cancellous tissue from an allograft plug having a cylindrically—shaped stalk. Referring to FIG. 17, the cannulated burring shell 260 has a hollow conical shell body 262 with a guide aperture 264 disposed through the tip of the cone to provide the cannulated feature. The cannulated burring shell 264 can also include a circular burring disk 266 that extends annularly outward from the base of the conical shell body 262. The interior surface of the conical shell body 262 and the underside of the burring disc 266 are adapted to grate or remove cannellous bone tissue.

In order to utilize the cannulated feature of the burring shell to facilitate proper shaping of the conical stalk, referring to FIG. 18, the specially adapted sleeve 270 is first placed about the cylindrical allograft plug 130. The sleeve 270 includes a tubular sleeve body 272 and a base plate 274 having a centrally located guide aperture 276 disposed therein. The sleeve 270 is placed about the allograft plug 130 such that the tubular sleeve body 272 receives the cylindrical cancellous stalk 134. Another elongated guide pin 278 is inserted through the guide aperture 276 and partially into the cancellous tissue of the stalk 134 as illustrated. Due to the concentric relation of the guide aperture and the tubular sleeve body 272, the guide pin 278 will be concentrically aligned within the cancellous stalk. The sleeve 270 can then be removed and the 1 burring shell 260 of FIG. 17, via its guide aperture 264, slide onto the guide pin so that the shell body 262 aligns with the cylindrical cancellous stalk. As can be appreciated, rotation of the cannulated burring shell 260 will remove cancellous tissue from the stalk and thereby form the conical shape. Furthermore, the burring disk 266 can remove or smooth the cancellous tissue on the underside of the allograft plug cartilage plate.

Figure 19:
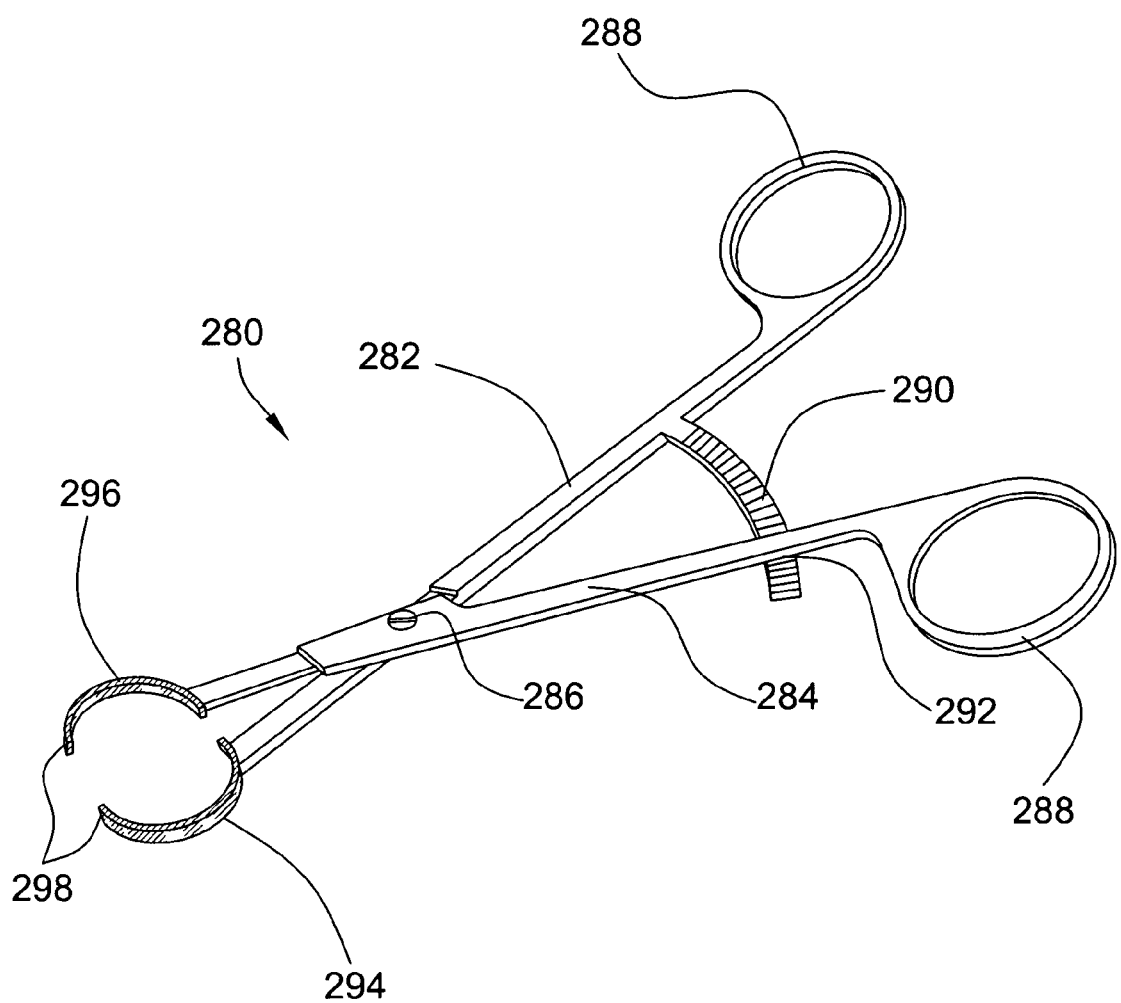
FIG. 19 is a perspective view of a pair of specially configured forceps for handling and manipulating a shaped allograft plug.

To handle a shaped allograft plug, especially a cylindrically or conically shaped plug, a pair of specially configure forceps can be provided. Referring to FIG. 19, the forceps 280 can include first and second lever arms 282, 284 that intersect and are pivotally joined at a pivot point 286. To grasp and manipulate the forceps, there is formed at the proximal end of each lever arm an eyelet 288 that can accommodate an operators fingers. Traversing the first lever arm 282 is a locking arm 290 that can engage a locking mechanism 292 on the second arm 284 so as to control and fix articulation of the forceps 280. The forceps 280 can be made from any suitable material such as, for example, stainless steel.

Formed at the working ends of the first and second lever arms 282, 284 are curved or semicircular clamps 294, 296. The clamps 294, 296 can be joined to the respective lever arms 282, 284 at any suitable angle such as, for example, in-line with the lever arms or at right angles with the lever arms. To prevent damaging the allograft plug, a suitable soft material 298 such as an elastomer can be coated onto the clamps 294, 296. Preferably the elastomer material can be silicone rubber. Hence, when handling a cylindrical or conical allograft plug, the curved clamps 294, 296 can be placed around the cartilage plate or cancellous stalk with the elastomer 298 protecting the bone tissue.

Figure 20:
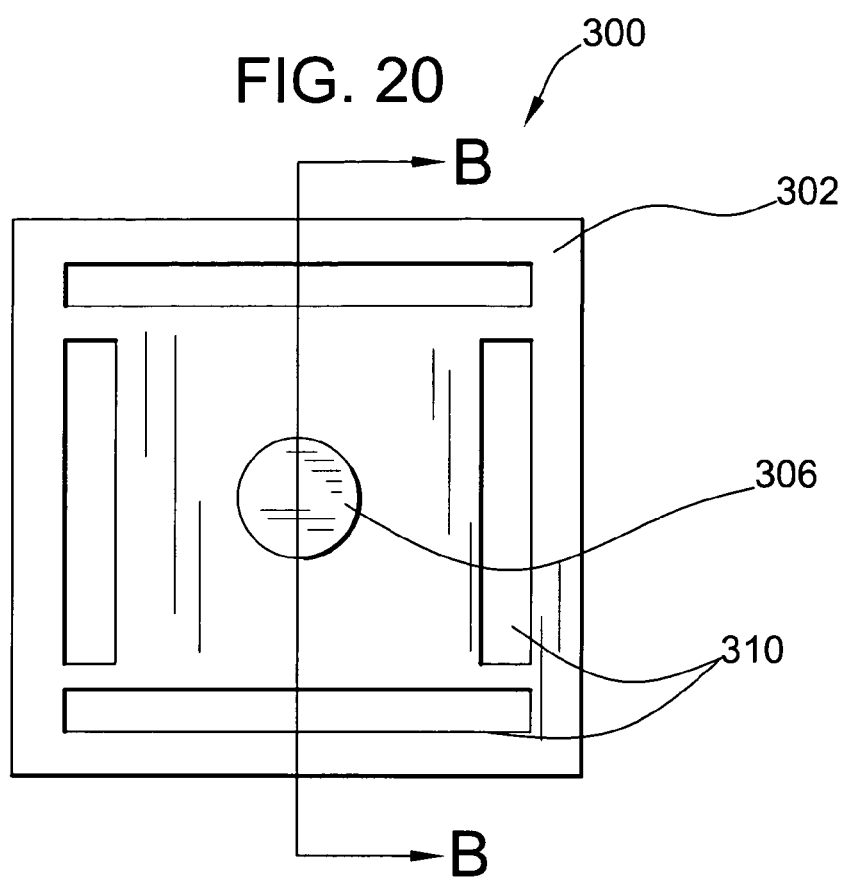
FIG. 20 is a front elevational view of a template having cut slots for removing and shaping a rectilinear allograft plug from a donor bone.
Figure 21:
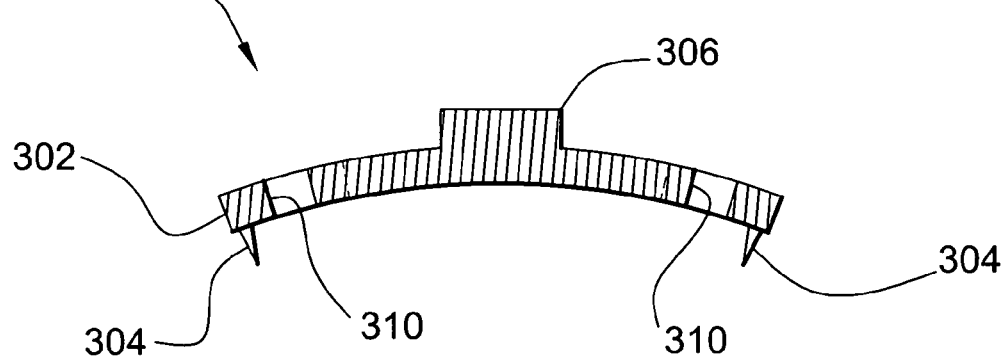
FIG. 21 is a cross-sectional view of the template taken along line B-B of FIG. 20.

To produce a rectilinear shaped allograft plug, such as the rectangular plug illustrated in FIG. 4, a special template 300 as illustrated in FIGS. 20 and 21 can be used. The template 300 includes a plate 302 having a cambered or curved shaped to adapt the plate for attachment to the condyle surface of a donor bone. Protruding from one surface of the plate 302 are a plurality of sharp teeth 304 to assist in attaching the template to the donor bone. The template 300 can further include an engagement structure 306 on the plate surface opposite the protruding teeth 304 to engage a detachable handle as described above. Furthermore, while the illustrated template 300 has a rectangular shape, in other embodiments the template can have other suitable shapes depending upon the shape of the allograft plug desired.

To actually remove the allograft plug, there is disposed through the plate 302 and within the perimeter outlined by the sharp teeth 304 a plurality of elongated cut slots 310 that are adapted to accommodate a osteotome, chisel, oscillating saw, or other cutting device. To produce a rectangular allograft plug, the illustrated cut slots 310 are arranged rectangularly. However, in other embodiments, to produce other shaped allograft plugs, such as triangular, the cut slots can be arranged in other patterns, such as triangularly. The cut slots 310 are furthermore disposed into the template 300 on a converging angle such that, when a cutting device is inserted through the cut slots and into the donor bone, the cuts being made will intersect at a point in the cancellous bone tissue. Intersecting the cuts will detach the allograft plug from the donor bone and simultaneously shape the allograft plug and its cancellous stalk. Hence, locating the cut slots 310 within the outline of the teeth 304 enables insertion of the teeth into the donor bone without damaging the healthy cartilage on allograft plug.

Figure 22:
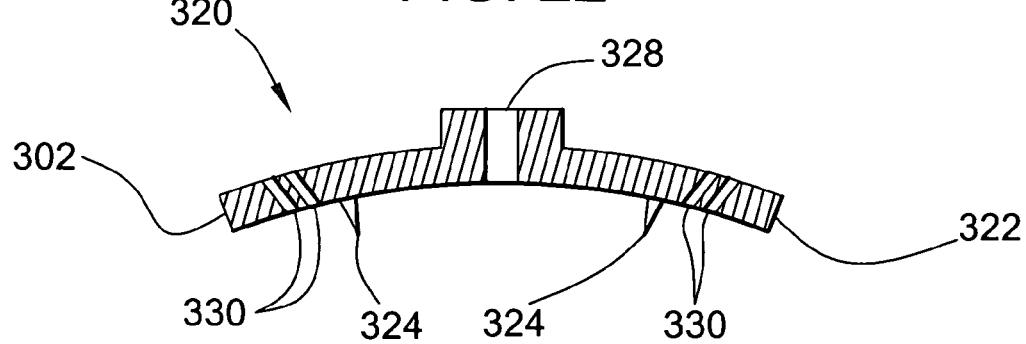
FIG. 22 is a cross-sectional view of another embodiment of a template, similar to the template shown in FIGS. 20 and 21, but adapted for preparing a recipient site on a host bone to receive a rectilinear allograft plug.

To prepare a recipient site for receiving an rectilinear allograft plug, a template 320 as illustrated in FIG. 22 can be used. The plate 322 of the template 320 is similar in shape and configuration to the template 300 of FIGS. 20 and 21 and also includes a plurality of cut slots 330 disposed angularly there through. To form a cutout in the host bone, the template 320 can be attached to the host bone at a location corresponding to a cartilage defect by utilizing the sharp teeth 324 protruding from the plate 322. To avoid damaging healthy cartilage on the host bone, the cut slots 330 are preferably located outside of the outline of the teeth 324. After attachment, various suitable cutting devices can be inserted through the cut slots 330 and into the donor bone to form the cutout. In an embodiment, to enable installation of the guide pin into the recipient site for aligning subsequent operations, the template 320 can have a guide aperture 328 disposed through the plate 322 generally central of teeth 324 and the cut slots 330.

As will be appreciated from the foregoing, the procedures and instruments described may also be applicable to the preparation and transplantation of a shaped autograft plug. For example, the removal, shaping, and insertion of an autograft plug from a host site and into a recipient site within the same patient is readily applicable with respect to rectilinear autograft plugs and can be performed using the same instruments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of preparing an osteochondral allograft, the method comprising:
   (i) removing from a donor site an allograft plug having a cartilage plate and cancellous bone tissue extending therefrom comprising:
      (a) attaching a guide plate to a donor bone at a location opposite the donor site, the guide plate having a first guide cylinder having a first bore and a second guide cylinder having a second bore, the second guide cylinder removably insertable into the first guide cylinder;
      (b) inserting a first crown saw having a first diameter through the second bore and into the donor bone a first depth to a point proximate the cartilage plate of the donor site;
      (c) removing the second guide cylinder from the first guide cylinder; and
      (d) inserting a second crown saw having a second diameter, wherein the second diameter is different than the first diameter, through the first bore a distance beyond the first depth across the donor bone and through the cartilage plate of the donor site to detach a portion of bone tissue from the donor bone; and
   (ii) shaping the allograft plug to remove cancellous bone tissue to form a cancellous stalk.

2. A method of preparing and transplanting an osteochondral allograft, the method comprising:
   (i) removing from a donor site an allograft plug having a cartilage plate and cancellous bone tissue extending therefrom comprising:
      (a) attaching a guide plate to a donor bone at a location opposite the donor site, the guide plate having a first guide cylinder having a first bore and a second guide cylinder having a second bore, the second guide cylinder removably insertable into the first guide cylinder;
      (b) inserting a first crown saw having a first diameter through the second bore and into the donor bone a first depth to a point proximate the cartilage plate of the donor site;
      (c) removing the second guide cylinder from the first guide cylinder; and
      (d) inserting a second crown saw having a second diameter, wherein the second diameter is different than the first diameter, through the first bore a distance beyond the first depth across the donor bone and through the cartilage plate of the donor site to detach a portion of bone tissue from the donor bone;

(ii) shaping the allograft plug to remove cancellous bone tissue to form a cancellous stalk;

(iii) preparing a recipient site on a host bone including forming a cutout into the bone at a location corresponding to a cartilage defect, the shape of the cutout generally corresponding to the shape of the allograft plug; and (iv) inserting the allograft plug into the cutout.

3. The method of claim 2, wherein preparing a recipient site comprises:

(v) providing a template having a guide aperture disposed there-through;

(vi) attaching the template to the host bone at a location corresponding to the cartilage defect;

(vii) inserting a guide pin through the guide aperture and into the host bone;

(viii) removing the template from the recipient site;

(ix) sliding onto the guide pin a cannulated drill bit, burr, or cutting disc; and (x) cutting the drill bit, burr, or cutting disc into the host bone to form the cutout.

4. The method of claim 3, wherein the cannulated drill bit, burr, or cutting disc has a counterbore forming element at the proximal end and a cutting body extending from the counterbore forming element.

5. The method of claim 4, wherein the cutting body is cylindrical or conical.

6. The method of claim 1 wherein inserting the second crown saw comprises inserting the second crown saw having a diameter that is greater than the first crown saw.

7. A method of preparing an osteochondral allograft, the method comprising:

(i) removing from a donor site an allograft plug having a cartilage plate and cancellous bone tissue extending therefrom comprising:

(a) attaching a guide plate to a donor bone at a location opposite the donor site, the guide plate having a first guide cylinder having a first bore and a second guide cylinder having a second bore, the second guide cylinder removably insertable into the first guide cylinder;

(b) inserting a first crown saw having a first diameter through the second bore and into the donor bone creating a first cylindrical bone portion from the donor bone within a perimeter of the first crown saw;

(c) removing the second guide cylinder from the first guide cylinder; and (d) inserting a second crown saw having a second diameter, wherein the second diameter is different than the first diameter, through the first bore across the donor bone and through the cartilage plate of the donor site to detach a portion of bone tissue from the donor bone, wherein inserting the second crown saw creates a second cylindrical bone portion from the donor bone within a perimeter of the second crown saw; and (ii) shaping the allograft plug to remove cancellous bone tissue to form a cancellous stalk.

8. The method of claim 7 wherein inserting the first crown saw comprises inserting the first crown saw into the donor bone a first depth to a point proximate the cartilage plate of the donor site and wherein inserting the second crown saw comprises inserting the second crown saw a distance beyond the first depth across the donor bone and through the cartilage plate of the donor site to detach a portion of bone tissue from the donor bone.

9. The method of claim 7 wherein inserting the second crown saw includes inserting the second crown saw having a larger diameter than the first crown saw.

10. A method of transplanting an osteochondral allograft, the method comprising:

(a) attaching a guide plate to donor bone at a location opposite a donor site, the guide plate having a first guide cylinder having a first bore and a second guide cylinder having a second bore, the second guide cylinder removably insertable into the first guide cylinder;

(b) cutting partially through a thickness of donor bone a first depth to a point proximate a cartilage plate of the donor site with a first crown saw along a cutting axis, the first crown saw having a first perimeter, wherein donor bone occupying a space within the first perimeter of the first crown saw is uncut;

(c) removing the second guide cylinder from the first guide cylinder;

(d) cutting entirely through the thickness of the donor bone through the first bore a distance beyond the first depth across the donor bone and through the cartilage plate of the donor site with a second crown saw along the cutting axis, the second crown saw having a second perimeter, the second perimeter being different than the first perimeter, wherein donor bone occupying a space within the second perimeter of the second crown saw is uncut creating an allograft plug;

(e) preparing a recipient site on a host bone including forming a cutout into the bone at a location corresponding to a cartilage defect, the shape of the cutout generally corresponding to the shape of the allograft plug and including a first portion corresponding to the first perimeter and a second portion corresponding to the second perimeter; and (f) inserting the allograft plug into the cutout.

11. The method of claim 10, wherein shaping the allograft plug further comprises trimming the length of the detached portion of bone tissue.

12. The method of claim 10, wherein inserting the first crown saw comprises inserting the first crown saw into the donor bone to a point 3 millimeters or less from the cartilage plate of the donor site.

* * * * *

UNITED STATES PATENT AND TRADEMARK OFFICE
CERTIFICATE OF CORRECTION

PATENT NO. : 7,371,260 B2
APPLICATION NO. : 11/259749
DATED : May 13, 2008
INVENTOR(S) : Theodore I. Malinin It is certified that error appears in the above-identified patent and that said Letters Patent is hereby corrected as shown below:

Column 1
Line 16, "as a" should be -- as an --.
Line 24, "2" should be -- underlying --.

Column 2
Line 62, after "template", insert -- . --.

Column 3
Line 14, "an" should be -- a --.

Column 5
Line 56, "pull" should be -- pulled --.

Column 6
Line 43, "Overtime" should be -- Over time --.

Column 7
Line 1, after "than", delete "the".

Column 8
Line 19, "1" should be -- cannulated --.
Line 28, "configure" should be -- configured --.
Line 34, "operators" should be -- operator's --.
Line 56, "shaped" should be -- shape --.

UNITED STATES PATENT AND TRADEMARK OFFICE
CERTIFICATE OF CORRECTION

PATENT NO. : 7,371,260 B2
APPLICATION NO. : 11/259749
DATED : May 13, 2008
INVENTOR(S) : Theodore I. Malinin It is certified that error appears in the above-identified patent and that said Letters Patent is hereby corrected as shown below:

<u>Column 9</u>
Line 2, "a" should be -- an --.
Line 18, "an" should be -- a --.

Signed and Sealed this

Sixteenth Day of December, 2008

JON W. DUDAS
*Director of the United States Patent and Trademark Office*